United States Patent [19]

Miura et al.

[11] Patent Number: 6,124,429
[45] Date of Patent: *Sep. 26, 2000

[54] GENETICALLY ENGINEERED ALPHA HELIX POLYPEPTIDE

[76] Inventors: Kin-ichiro Miura; Shuichi Kojima; Yukino Kuriki; Takao Yoshida; Susumu Nakae; Yoko Doi, all of c/o Institute for Biomolecular Science, Faculty of Science, Gakushu-in University, 1-5-1, Meijiro, Toshima-ku, Tokyo 171, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/752,526

[22] Filed: Nov. 20, 1996

[30] Foreign Application Priority Data

Apr. 10, 1996 [JP] Japan ................................. 8-113128

[51] Int. Cl.$^7$ ..................................................... G03C 5/00
[52] U.S. Cl. ............................ 530/324; 530/300; 530/326
[58] Field of Search ........................ 435/69.1; 530/324, 530/325, 326, 327, 328, 300, 330

[56] References Cited

U.S. PATENT DOCUMENTS

| | | | |
|---|---|---|---|
| 4,514,331 | 4/1985 | Kaiser et al. ........................ | 260/112.5 |
| 4,835,252 | 5/1989 | Musso et al. ........................ | 530/324 |
| 4,939,224 | 7/1990 | Musso et al. ........................ | 530/324 |
| 5,374,531 | 12/1994 | Pang et al. ........................ | 424/486 |
| 5,789,542 | 8/1998 | McLaughlin et al. ................ | 530/326 |

OTHER PUBLICATIONS

Chou et al. "Empirical predictions of protein conformation" Ann. Rev. Biochem. 47, 251–276, 1978.

Kaiser et al. "Secondary structure of proteins and peptides in amphiphlic enviroments (a review)" Proc. Natl. Acad. 80, 1137–1143, Feb. 1983.

Moe et al, "Design, synthesis, and characterization of a model peptide having potent calcitonin–like biological activity: implications for calcitonin structure/activity" Biochemistry 24, 1971–1976, 1985.

Minakata et al, "Characteristics of amphiphilic secondary structures in neuopeptide Y through the design, synthesis and study model peptides" J. Biol. Chem 264, 7907–7913, May 1989.

*Primary Examiner*—Nashaat Nashed
*Attorney, Agent, or Firm*—Morrison & Foerster, LLP

[57] ABSTRACT

A polypeptide having α-helix structure, which has a hydrophilic surface and a hydrophobic surface, and which is produced by genetic engineering techniques is disclosed. According to the present invention, stable polypetide molecules having α-helix structure, which have a constant molecular weight and which can be used in various applications represented by materials for medical applications, can be provided.

2 Claims, 4 Drawing Sheets

GENETICALLY ENGINEERED ALPHA HELIX POLYPEPTIDE

FIELD OF THE INVENTION

The present invention relates to a polypeptide and a fibrous association consisting essentially of the same.

DESCRIPTION OF THE RELATED ART

The α-helix is one of the secondary structures of proteins and polypeptides, which consists of regular helical array of 3.6 amino acid residues per turn. In α-helix, hydrogen bonds are formed among the —NH— and —CO— groups of every four amino acid residues, and are substantially parallel to the axis of the helix. Thus, the α-helix has a structure with an energetically high stability. Helical structure includes two types of helices, that is, right-handed helix and left-handed helix. However, because of stability, only the right-handed helix occurs in nature.

Properties and stability of α-helix are being studied by substituting the amino acid residues in α-helix of proteins and by using chemically synthesized polypeptides. However, by these methods, it is difficult to control the molecular weight of the α-helix.

Unless polypeptide molecules have the same amino acid sequence and the same length, association of the molecules is non-uniform, so that association polypeptides which are long and have specific properties cannot be obtained.

SUMMARY OF THE INVENTION

An object of the present invention is to provide a polypeptide by genetic engineering techniques, by which polypeptide stably forms α-helix and has a constant length.

The present invention provides a polypeptide having α-helix structure, which has a hydrophilic surface and a hydrophobic surface, and which is produced by genetic engineering techniques. The present invention also provides a fibrous protein consisting essentially of the polypeptide according to the present invention.

DETAILED DESCRIPTION OF THE PREFERRED EMBODIMENTS

Figure 1:
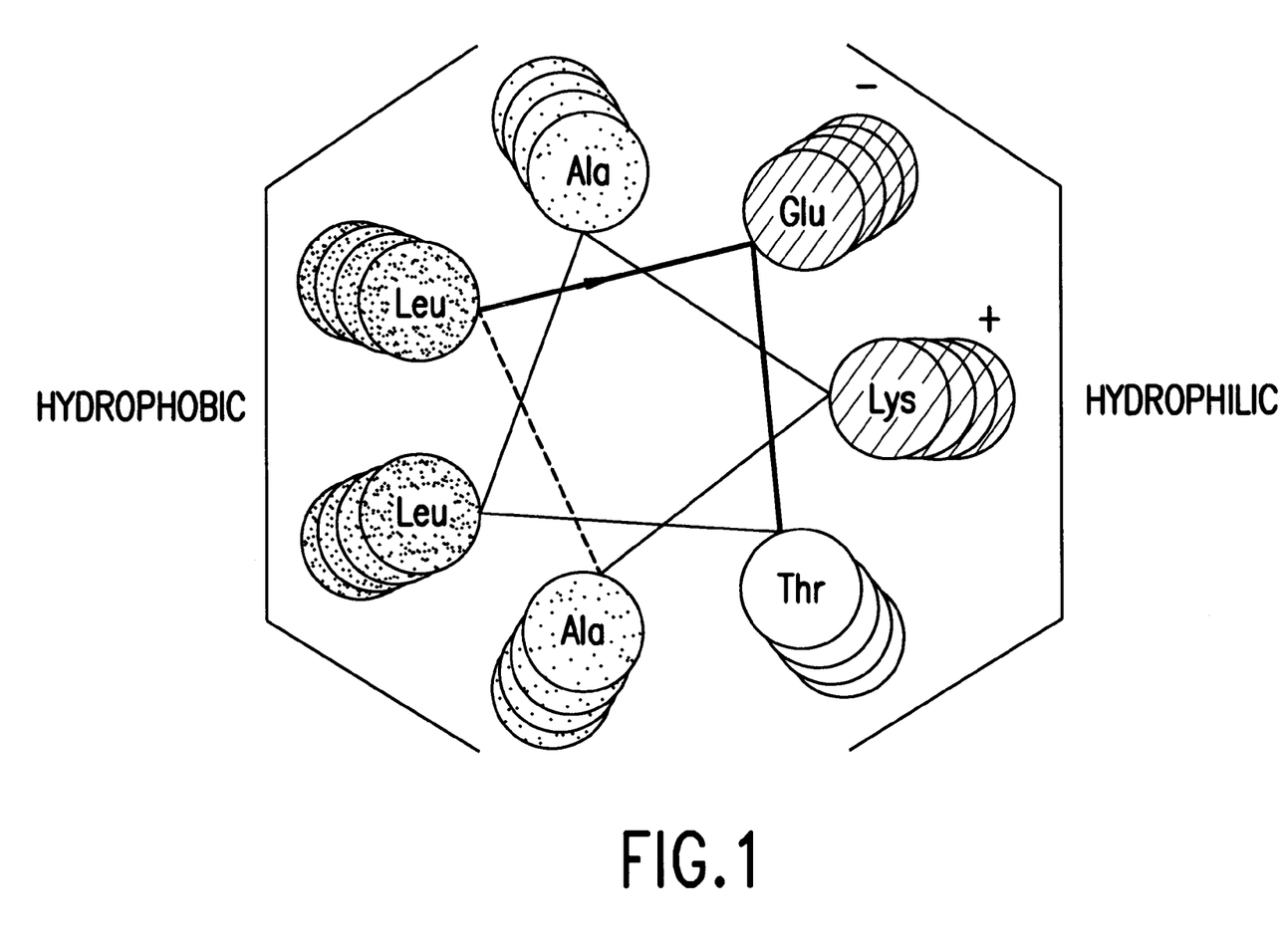
FIG. 1 is a sectional view of α-helix structure of α3 which is an embodiment of the present invention.

As shown in FIG. 1, the polypeptide according to the present inveiltion has hydrophobic amino acid residues and hydrophilic amino acid residues in its amino acid sequence, so that it has a hydrophobic surface and a hydrophilic surface in α-helix. Thus, the α-helix is amphipathic.

Referring to FIG. 1, for example, the polypeptide has an amino acid sequence of Leu-Glu-Thr-Leu-Ala-Lys-Ala-Leu-Glu-Thr-Leu-Ala-Lys-Ala-Leu-Glu-Thr-Leu-Ala-Lys-Ala-Leu-Glu-Thr-Leu-Ala-Lys-Ala-Leu-Glu-Thr-Leu-Ala-Lys-Ala which contains 4 repeats of a sequence consisting of 7 amino acid residues, and the Leu residues (in SEQ ID NO. 5 following the initial Met residue) of 1st, 8th, 15th and 22nd residues in the sequence are arranged such that they are placed on the same side of the α-helix. Thus, the α-helix has a hydrophobic surface and a hydrophilic surface in the side surface thereof thereby forming stable α-helix structure.

To make the α-helix have a hydrophobic surface, it is preferred that the polypeptide according to the present invention have at least one amino acid residue selected from the group consisting of Leu, Ala and Val. It is more preferred that adjacent two or more amino acid residues in the sectional view be selected from this group of amino acid residues, as shown in FIG. 1.

Similarly, to make the α-helix have a hydrophilic Surface, it is preferred that the polypeptide according to the present invention have at least one amino acid residue selected from the group consisting of Glu, Lys and Thr. It is more preferred that adjacent two or more amino acid residues in the sectional view be selected from this group of amino acid residues, as shown in FIG. 1.

Among the polypeptides mentioned above, the polypeptide of the present invention preferably has amino acid residues of Lys, Glu, Ala, Thr and Leu.

One of the characteristic features of the polypeptide according to the present invention is that it has a hydrophilic surface and a hydrophobic surface along the longitudinal direction of the α-helix. As long as the polypeptide has a hydrophilic surface and a hydrophobic surface in the side surface of the α-helix, the amino acid sequence is not restricted. Since α-helix consists of regular helical array ol 3.6 amino acid residues per turn, stable α-helix can be formed by repeating a unit consisting of 7 amino acid residues. Thus, it is preferred that the polypeptide according to the present invention have repeating units each of which consists essentially of 7 amino acid residues, and it is preferred that the polypeptide have not less than 3 such repeating units.

A preferred example of the repeating unit in the polypeptide according to the present invention contains the amino acid sequence shown in SEQ ID NO. 1. Examples of such a polypeptide include the polypeptide (SEQ ID NO. 3, hereinafter referred to as "α3") comprising three repeats of this amino acid sequence, the polypeptide (SEQ ID NO. 5, herein after referred to as "α4") comprising four repeats of this amino acid sequence, the polypeptide (SEQ ID NO. 7, hereinafter referred to as "r'3") having the sequence which is reverse to the sequence of α3, and the polypeptide (SEQ ID NO. 9, hereinafter referred to as "r3") having the same amino acid sequence as r'3 except that the sequence is shifted by 4 residues.

In addition to the polypeptides which comprise only the repeating units consisting essentially of 7 amino acid residues, the polypeptide according to the present invention may comprise one or more linkers inserted between the repeating units consisting essentially of the 7 amino acid residues. Examples of the linker include polypeptides having 5–7 amino acid residues. The amino acid sequence to be inserted may be appropriately selected from the view point of flexibility. A preferred example of the linker has a sequence of -Gly-Pro-Arg-Arg-Gly-SEQ ID NO: 13. A preferred example of the polypeptide containing this linker is the polypeptide (SEQ ID NO. 11, hereinafter referred to as α3-GPRRG-α3) which comprises two α3 polypeptides ligated via the linker (Gly-Pro-Arg-Arg-Gly).

As can be seen from α3 shown in FIG. 1 and SEQ ID NO:3 as an embodiment, Leu residues (L1 and L4) form a hydrophobic surface and Glu and Lys residues (E2, K6) form a hydrophilic surface, so that α3 is amphipathic.

Therefore, α3 molecules can stably associate maintaining α-helix. Especially, in cases where the Polypeptide comprises not less than 4 repeating units, the polypeptide molecules can stably associate maintaining α-helix structure without substantially being influenced by pH and salt concentration.

Since the polypeptide according to the present invention forms amphipathic α-helix as mentioned above, it can associate to form a fibrous association. The diameter of the α-helix is about 1 nm and that of tile association may be, although not restricted, not less than several nanometers.

The polypeptide according to the present invention is prepared by the genetic recombination technique described below. That is, the polypeptide may be produced by transforming host cells with an expression vector containing the DNA encoding the polypeptide according to the present invention, and culturing the obtained transformants.

As the vector, an expression plasmid pMKAK3 (Kumagai, I., Takeda, S., and Miura, K. (1990), Protein Engng. 5, 449–452) containing the porcine adenylate kinase gene may preferably be employed, although the vector is not restricted thereto.

As the host cells, although E. coli cells may be used, other cells may also be used.

According to the present invention, stable polypeptide molecules having α-helix structure, which have a constant molecular weight can be produced by genetic engineering techniques, so that polypeptides having α-helix structure, which may be used in various applications such as materials for medical applications, are provided.

Although the use of the polypeptides according to the present invention is not restricted, they may be used as a carrier of various drugs in drug delivery system, by enclosing the drugs in the α-helix to form clathrates. They may also be used as various markers by incorporating fluorescent tyrosine residues or the like in the polypeptide.

The associations of the polypeptides according to the present invention may be used as biocompatible polymer materials, including materials for medicine such as surgical sutures, artificial blood vessels and artificial tissues.

EXAMPLES

The present invention will now be described by way of examples thereof. However, the present invention is not restricted by the examples.

Example 1
Construction of Expression Plasmid

Each of the polynucleolide sequences shown in SEQ ID NOs. 2, 4, 6, 8, and 10 was inserted into a plasmid pMKAK3 (Kumagai, I., Takeda, S., and Miura, K. (1990). Protein Engng. 5, 449–452) to obtain 5 types of expression plasmids.

Example 2
Expression and Purification of Polypeptide

E. coli JM109 cells were transformed with an expression vector containing the nucleotide sequence shown in SEQ ID NO. 4 and the obtained transformants were cultured in 5.8 liters of LB/ampicillin medium. After incubation at 37°C. for about 15 hours, the cells were collected and washed with TE buffer. The cells were disrupted by ultrasonication (200 W, 20 kHz) and the resultant was centrifuged (100,000 rpm, 10 min., 4° C.), followed by recovering insoluble inclusion bodies. The obtained inclusion bodies were washed with TE buffer until the supernatant after centrifugation became transparent.

The recovered inclusion bodies were dissolved in 42 ml of 70% formic acid, and 1% mercaptoethanol and 2% cyanoge bromide were added, followed by incubation overnight at 37° C. twice. Whether the desired polypeptide was detached from the porcine adenylate kinase was checked by SDS-PAGE. The obtained proteins were dialyzed against distilled water and 10 mM Tris-HCl (pH 8.5). The dialyzed proteins were subjected to anion-exchange chromatography (DEAE-cellulose) and eluted with 10 mM Tris-HCl (pH 8.5) and 0.5 M NaCl at a flow rate of 1 ml/min. Fractions of 5 ml each were collected, and absorbances at 230 nm and 280 nm of each fraction were measured.

The fractions which exhibited absorption at 230 nm were subjected to reverse phase HPLC and peak which has an absorption at 230 nm alone was collected. The collected fraction was two-fold diluted with distilled water and the resultant was lyophilized to obtain a material in the form of white cotton. Amino acid analysis was performed using 5 μl aliquot of the obtained material, to find that 5.9 μmol of α4 was obtained from 5.8 liters of medium.

Example 3

The same procedure as in Example 2 was repeated except that an expression vector containing the nucleotide sequence shown in SEQ ID NO. 2 was used in place of the expression vector used in Example 2 to obtain α3; except that an expression vector containing the nucleotide sequence shown in SEQ ID NO. 6 was used to obtain r'3; except that an expression vector containing the nucleotide sequence shown in SEQ ID NO. 8 was used to obtain r3; or except that an expression vector containing the nucleotide sequence shown in SEQ ID NO. 10 was used to obtain α3-GPRRG-α3: in an amount of 2–10 mg from 1 liter of medium, respectively.

Figure 2:
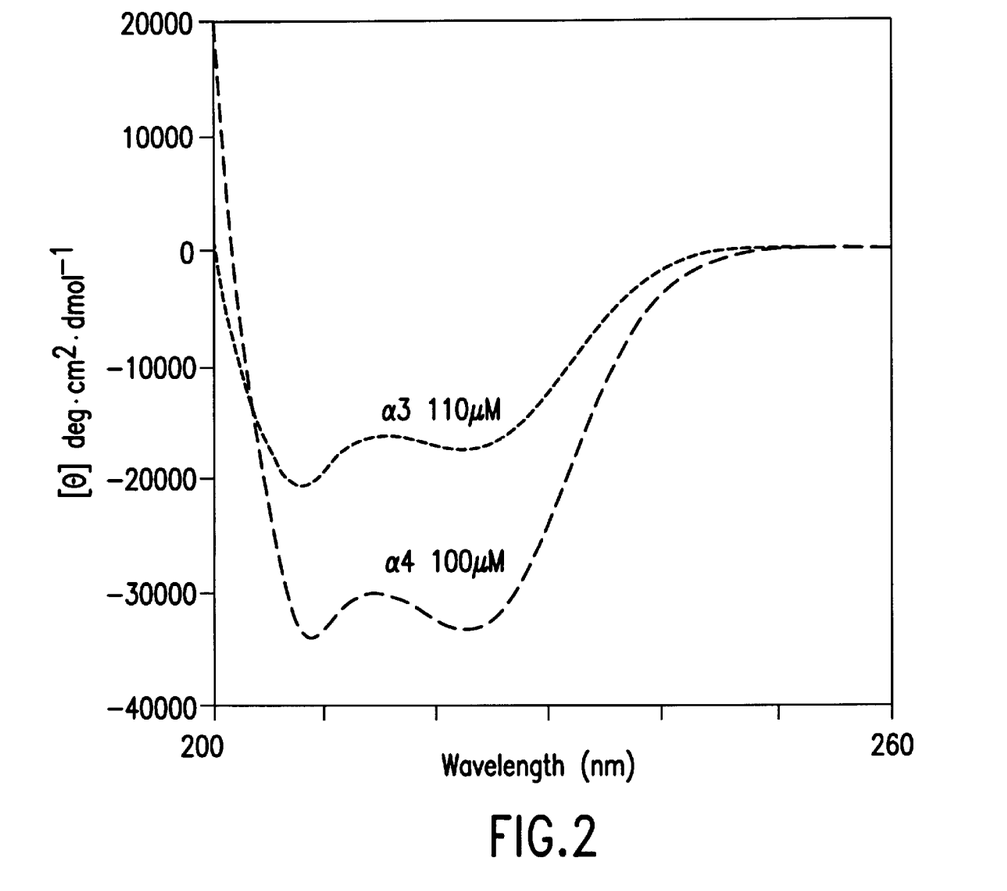
FIG. 2 shows the results of CD spectra of α3 and α4 in Example 4.
Figure 3:
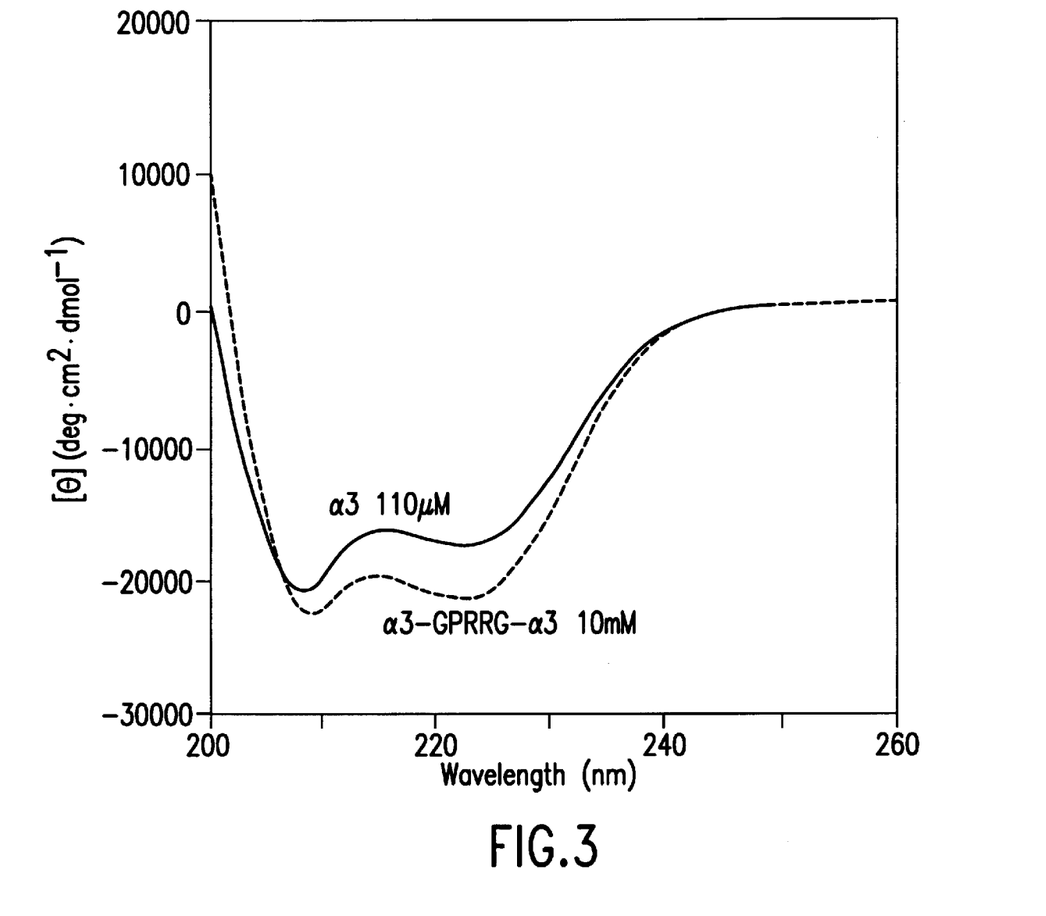
FIG. 3 shows the results of CD spectra of α3 and α3-GPRRG-α3 in Example 4.
Figure 4:
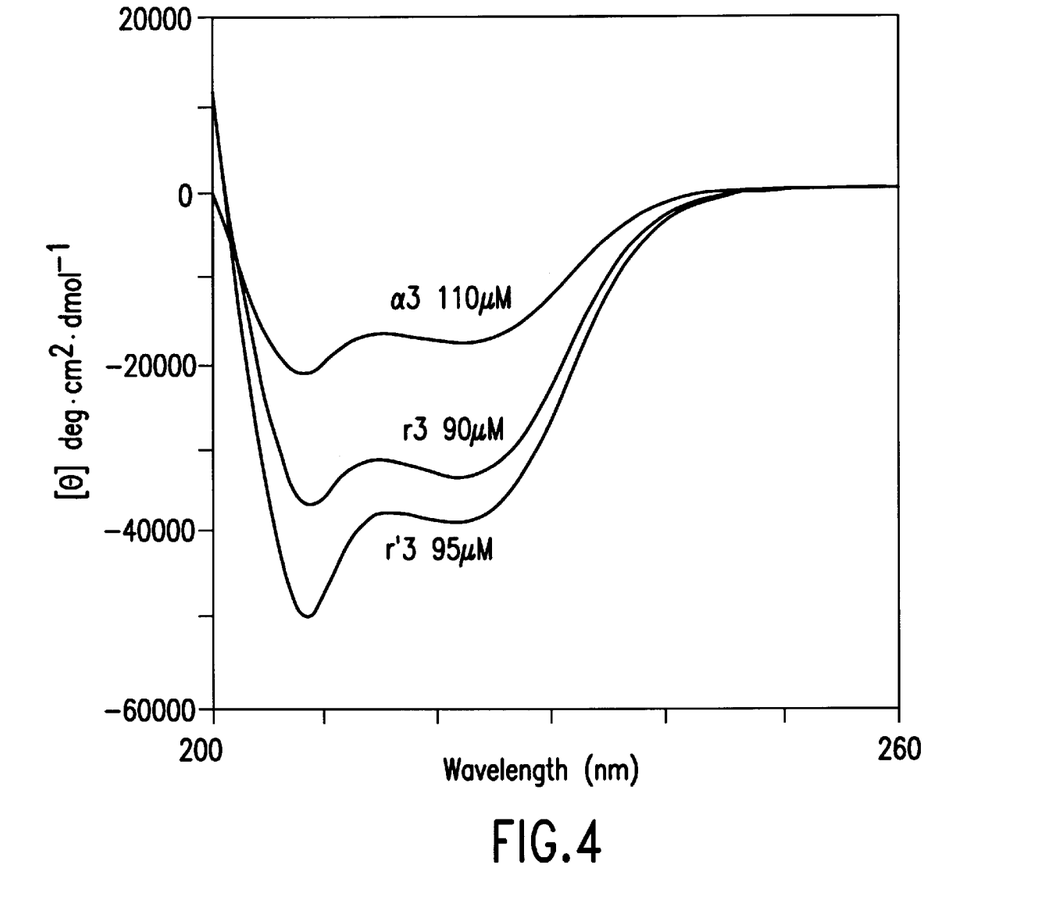
FIG. 4 shows the results of CD spectra of α3, r3 and r'3 in Example 4.

Example 4
Confirmation of α-helix

α4 obtained in Example 2 or α3 obtained in Example 3 was dissolved at a concentration of 100 μM or 110 μM, respectively, in It) mM phosphate buffer (pH6.0) containing 0.1 M KCl, and CD spectra of the obtained solutions were measured using Jasco-J720 CD spectrophotometer at 30° C. The light pass length in the cell was 1 mm. The results are shown in FIG. 2. As is apparent from FIG. 2, spectra halving relative minimums at 208 nm and 222 nm, characteristic to α-helix, were obtained for both α3 and α4. The CD spectra of α3 (110 μM and α3-GPRRG-α3 (10 μM) measured under the same conditions as mentioned above are shown in FIG. 3. The CD spectra of α3 (110 μM), r3 (90 μM) and r'3 (95 μM) measured under the same conditions as mentioned above are shown in FIG. 4. It is seen from FIG. 3 that α3-GPRRG-α3 exists more stably than α3. This is presumably because that the number of the repeating units consisting of 7 amino acid residues in α3-GPRRG-α3 is 6 in contrast to 3 in α3, so that interaction between the hydrophobic surfaces of α-helix of α3-GPRRG-α3 is stronger than that of α3 in spite of the existence of the linker consisting of 5 amino acid residues between two α3 moieties. It is seen film FIG. 4 that r'3 and r3 form α-helix more stably than α3. This is presumably because intramolecular and intermolecular electrostatic interactions of the polypeptide molecules contribute to stabilization of α-helix.

Example 5

Aqueous solutions of α4, α3, r3, r3', α3-GPRRG-α3 obtained in Example 2 or 3 were observed with a transmission electron microscope. As a result, it was observed that elongated fibrous associations were formed for all of the 5 types of peptides.

We claim:

1. An isolated and purified polypeptide having an amino acid sequence shown in SEQ ID NO. 3, 5, 7, 9, 11 or 12.

2. A fibrous protein comprising the polypeptide of claim 1.

\* \* \* \* \*

```
                          SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
           (A) LENGTH: 7 amino acids
           (B) TYPE: amino acid
           (C) STRANDEDNESS: Not Relevant
           (D) TOPOLOGY: linear (ii) MOLECULE TYPE: protein (xi) SEQUENCE DESCRIPTION: SEQ ID NO:1:

Leu Glu Thr Leu Ala Lys Ala
1               5

(2) INFORMATION FOR SEQ ID NO:2:

(i) SEQUENCE CHARACTERISTICS:
           (A) LENGTH: 78 base pairs
           (B) TYPE: nucleic acid
           (C) STRANDEDNESS: single
           (D) TOPOLOGY: linear (ix) FEATURE:
           (A) NAME/KEY: CDS
           (B) LOCATION: 6..71

(xi) SEQUENCE DESCRIPTION: SEQ ID NO:2:

AATTC ATG CTG GAA ACC CTG GCG AAG GCT CTG GAG ACC CTG GCG AAG            47
      Met Leu Glu Thr Leu Ala Lys Ala Leu Glu Thr Leu Ala Lys
        1               5                  10
GCT CTG GAA ACC CTG GCT AAA GCT TGATAGG                                  78
Ala Leu Glu Thr Leu Ala Lys Ala
 15                  20

(2) INFORMATION FOR SEQ ID NO:3:

(i) SEQUENCE CHARACTERISTICS:
           (A) LENGTH: 22 amino acids
           (B) TYPE: amino acid
           (D) TOPOLOGY: linear (ii) MOLECULE TYPE: protein (xi) SEQUENCE DESCRIPTION: SEQ ID NO:3:

Met Leu Glu Thr Leu Ala Lys Ala Leu Glu Thr Leu Ala Lys Ala Leu
1               5                  10                  15

Glu Thr Leu Ala Lys Ala
            20

(2) INFORMATION FOR SEQ ID NO:4:

(i) SEQUENCE CHARACTERISTICS:
           (A) LENGTH: 99 base pairs
           (B) TYPE: nucleic acid
           (C) STRANDEDNESS: single
           (D) TOPOLOGY: linear
```

(ix) FEATURE:
              (A) NAME/KEY: CDS
              (B) LOCATION: 6..92

(xi) SEQUENCE DESCRIPTION: SEQ ID NO:4:

AATTC ATG CTG GAA ACC CTG GCG AAG GCT CTG GAG ACC CTG GCG AAG          47
      Met Leu Glu Thr Leu Ala Lys Ala Leu Glu Thr Leu Ala Lys
           25                  30                  35

GCT CTG GAA ACC CTG GCT AAA GCT CTG GAA ACC CTG GCG AAG GCT            92
Ala Leu Glu Thr Leu Ala Lys Ala Leu Glu Thr Leu Ala Lys Ala
             40                  45                  50

TGATAGG                                                                99

(2) INFORMATION FOR SEQ ID NO:5:

(i) SEQUENCE CHARACTERISTICS:
              (A) LENGTH: 29 amino acids
              (B) TYPE: amino acid
              (D) TOPOLOGY: linear (ii) MOLECULE TYPE: protein (xi) SEQUENCE DESCRIPTION: SEQ ID NO:5:

Met Leu Glu Thr Leu Ala Lys Ala Leu Glu Thr Leu Ala Lys Ala Leu
 1               5                  10                  15

Glu Thr Leu Ala Lys Ala Leu Glu Thr Leu Ala Lys Ala
             20                  25

(2) INFORMATION FOR SEQ ID NO:6:

(i) SEQUENCE CHARACTERISTICS:
              (A) LENGTH: 78 base pairs
              (B) TYPE: nucleic acid
              (C) STRANDEDNESS: single
              (D) TOPOLOGY: linear (ix) FEATURE:
              (A) NAME/KEY: CDS
              (B) LOCATION: 6..71

(xi) SEQUENCE DESCRIPTION: SEQ ID NO:6:

AATTC ATG GCT AAG GCG CTG ACC GAA CTG GCT AAG GCG CTG ACC GAG          47
      Met Ala Lys Ala Leu Thr Glu Leu Ala Lys Ala Leu Thr Glu
           30                  35                  40

CTG GCT AAA GCT CTG ACC GAA CTG TGATAGG                                78
Leu Ala Lys Ala Leu Thr Glu Leu
         45                  50

(2) INFORMATION FOR SEQ ID NO:7:

(i) SEQUENCE CHARACTERISTICS:
              (A) LENGTH: 22 amino acids
              (B) TYPE: amino acid
              (D) TOPOLOGY: linear (ii) MOLECULE TYPE: protein (xi) SEQUENCE DESCRIPTION: SEQ ID NO:7:

Met Ala Lys Ala Leu Thr Glu Leu Ala Lys Ala Leu Thr Glu Leu Ala
 1               5                  10                  15

Lys Ala Leu Thr Glu Leu
             20

(2) INFORMATION FOR SEQ ID NO:8:

(i) SEQUENCE CHARACTERISTICS:

(A) LENGTH: 78 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 6..71

(xi) SEQUENCE DESCRIPTION: SEQ ID NO:8:

```
AATTC ATG CTG ACC GAA CTG GCG AAG GCT CTG ACC GAG CTG GCG AAG      47
      Met Leu Thr Glu Leu Ala Lys Ala Leu Thr Glu Leu Ala Lys
          25                  30                  35

GCT CTG ACC GAA CTG GCT AAA GCT TGATAGG                            78
Ala Leu Thr Glu Leu Ala Lys Ala
            40
```

(2) INFORMATION FOR SEQ ID NO:9:

(i) SEQUENCE CHARACTERISTICS:
        (A) LENGTH: 22 amino acids
        (B) TYPE: amino acid
        (D) TOPOLOGY: linear (ii) MOLECULE TYPE: protein (xi) SEQUENCE DESCRIPTION: SEQ ID NO:9:

```
Met Leu Thr Glu Leu Ala Lys Ala Leu Thr Glu Leu Ala Lys Ala Leu
 1               5                  10                  15

Thr Glu Leu Ala Lys Ala
            20
```

(2) INFORMATION FOR SEQ ID NO:10:

(i) SEQUENCE CHARACTERISTICS:
        (A) LENGTH: 156 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 6..149

(xi) SEQUENCE DESCRIPTION: SEQ ID NO:10:

```
AATTC ATG CTG GAA ACC CTG GCG AAG GCT CTG GAG ACC CTG GCG AAG      47
      Met Leu Glu Thr Leu Ala Lys Ala Leu Glu Thr Leu Ala Lys
          25                  30                  35

GCT CTG GAA ACC CTG GCT AAG GCT GGT CCG CGT CGC GGC CTG GAG ACC    95
Ala Leu Glu Thr Leu Ala Lys Ala Gly Pro Arg Arg Gly Leu Glu Thr
            40                  45                  50

CTG GCT AAG GCT CTG GAG ACC CTG GCG AAG GCT CTG GAA ACC CTG GCT   143
Leu Ala Lys Ala Leu Glu Thr Leu Ala Lys Ala Leu Glu Thr Leu Ala
            55                  60                  65

AAA GCT TGATAGG                                                   156
Lys Ala
    70
```

(2) INFORMATION FOR SEQ ID NO:11:

(i) SEQUENCE CHARACTERISTICS:
        (A) LENGTH: 48 amino acids
        (B) TYPE: amino acid
        (D) TOPOLOGY: linear (ii) MOLECULE TYPE: protein (xi) SEQUENCE DESCRIPTION: SEQ ID NO:11:

```
Met Leu Glu Thr Leu Ala Lys Ala Leu Glu Thr Leu Ala Lys Ala Leu
 1               5                  10                  15

Glu Thr Leu Ala Lys Ala Gly Pro Arg Arg Gly Leu Glu Thr Leu Ala
                20                  25                  30

Lys Ala Leu Glu Thr Leu Ala Lys Ala Leu Glu Thr Leu Ala Lys Ala
            35                  40                  45
```

(2) INFORMATION FOR SEQ ID NO:12:

(i) SEQUENCE CHARACTERISTICS:
        (A) LENGTH: 35 amino acids
        (B) TYPE: amino acid
        (C) STRANDEDNESS: Not Relevant
        (D) TOPOLOGY: linear     (ii) MOLECULE TYPE: peptide     (xi) SEQUENCE DESCRIPTION: SEQ ID NO:12:

```
Leu Glu Thr Leu Ala Lys Ala Leu Glu Thr Leu Ala Lys Ala Leu Glu
 1               5                  10                  15

Thr Leu Ala Lys Ala Leu Glu Thr Leu Ala Lys Ala Leu Glu Thr Leu
                20                  25                  30

Ala Lys Ala
            35
```

(2) INFORMATION FOR SEQ ID NO:13:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear     (ii) MOLECULE TYPE: peptide     (xi) SEQUENCE DESCRIPTION: SEQ ID NO:13:

```
Gly Pro Arg Arg Gly
 1               5
```